(12) United States Patent
Rubin et al.

(10) Patent No.: US 10,478,547 B2
(45) Date of Patent: *Nov. 19, 2019

(54) IRRIGATION ASSEMBLY

(71) Applicant: Preva, LLC., Weston, FL (US)

(72) Inventors: Keith Rubin, Ft. Lauderdale, FL (US); Ken Solovay, New York, NY (US); James Layer, New York, NY (US); Alex Desimone, New York, NY (US)

(73) Assignee: PREVA, LLC., Weston, FL (US)

( * ) Notice: Subject to any disclaimer, the term of this patent is extended or adjusted under 35 U.S.C. 154(b) by 560 days.

This patent is subject to a terminal disclaimer.

(21) Appl. No.: 15/257,409

(22) Filed: Sep. 6, 2016

(65) Prior Publication Data

US 2016/0375192 A1    Dec. 29, 2016

Related U.S. Application Data

(63) Continuation-in-part of application No. 13/664,034, filed on Oct. 30, 2012, now Pat. No. 9,433,724.

(51) Int. Cl.
*A61M 3/02* (2006.01)

(52) U.S. Cl.
CPC ........ *A61M 3/0283* (2013.01); *A61M 3/0233* (2013.01); *A61M 3/0279* (2013.01); *A61M 2205/18* (2013.01); *A61M 2210/0618* (2013.01)

(58) Field of Classification Search
CPC .............. A61M 3/0283; A61M 3/0287; A61M 3/0279; A61M 3/0233; A61M 1/0058; A61M 16/0666; A61M 2210/0618
See application file for complete search history.

(56) References Cited

U.S. PATENT DOCUMENTS

| | | |
|---|---|---|
| 2,566,806 A | 9/1951 | Miller |
| 3,429,313 A | 2/1969 | Romanelli |

(Continued)

FOREIGN PATENT DOCUMENTS

| | | |
|---|---|---|
| CH | 691885 A5 | 11/2001 |
| EP | 197778 A1 | 8/2008 |

(Continued)

OTHER PUBLICATIONS

Translation EP-238918-A1, EPO Patent Translate, translated Mar. 2, 2019.*

(Continued)

*Primary Examiner* — Andrew M Gilbert
(74) *Attorney, Agent, or Firm* — Malloy & Malloy, P.L.

(57) ABSTRACT

An assembly structured for concurrent irrigation and aspiration of a nasal cavity including a housing having a supply container disposed therein for the removable retention of irrigating fluid. A nasal applicator comprises first and second passages respectfully structured to deliver irrigating fluid to the nasal cavity and concurrently remove waste fluid therefrom. An activating assembly includes a plunger biased into a continuous pressure applying, dispensing relation to the irrigating fluid and a valve assembly is selectively disposable into an open position facilitating fluid communication between the supply container and the applicator for the delivery of the irrigating fluid therethrough into the nasal cavity. The activating assembly is further structured to create a negative pressure within the chamber which communicates with the second passage of the applicator to facilitate delivery of the waste fluid therefrom along a path of travel to an interior of the chamber.

8 Claims, 11 Drawing Sheets

(56) References Cited

U.S. PATENT DOCUMENTS

| | | | |
|---|---|---|---|
| 4,294,251 A | 10/1981 | Greenwald et al. | |
| 4,457,747 A | 7/1984 | Tu | |
| 4,655,197 A | 4/1987 | Atkinson | |
| 4,663,628 A | 5/1987 | Duncan et al. | |
| 4,790,979 A | 12/1988 | Terminiello | |
| 4,904,238 A | 2/1990 | Williams | |
| 4,924,862 A | 5/1990 | Levinson | |
| 4,998,915 A | 3/1991 | Hannah | |
| 5,009,634 A | 4/1991 | Feldman et al. | |
| 5,277,175 A | 1/1994 | Riggs | |
| 5,505,193 A | 4/1996 | Ballini et al. | |
| 5,542,918 A | 8/1996 | Atkinson | |
| 5,649,530 A | 7/1997 | Ballini | |
| 6,022,748 A | 2/2000 | Charych et al. | |
| 6,135,358 A * | 10/2000 | Ballini | A61H 35/04 239/121 |
| 6,145,703 A | 11/2000 | Opperman | |
| 6,736,792 B1 | 5/2004 | Liu | |
| 6,907,879 B2 * | 6/2005 | Drinan | A61B 5/411 128/200.14 |
| 7,063,686 B2 | 6/2006 | Mezzoli | |
| 7,080,980 B2 | 7/2006 | Klupt | |
| 7,143,763 B2 | 12/2006 | Abate | |
| 7,569,031 B2 | 8/2009 | Britto | |
| 7,959,597 B2 | 6/2011 | Baker et al. | |
| 7,981,077 B2 | 7/2011 | Hoke et al. | |
| 8,048,023 B2 | 11/2011 | Hoke et al. | |
| 8,343,114 B2 | 1/2013 | Mehta | |
| 9,289,547 B2 | 3/2016 | Layer et al. | |
| 9,433,724 B2 * | 9/2016 | Rubin | A61M 3/0233 |
| 2003/0069549 A1 | 4/2003 | MacMahon et al. | |
| 2003/0089367 A1 | 5/2003 | Abate | |
| 2003/0158527 A1 | 8/2003 | Mezzoli | |
| 2003/0172925 A1 | 9/2003 | Zocca et al. | |
| 2004/0182388 A1 | 9/2004 | Djupesland | |
| 2005/0004498 A1 | 1/2005 | Klupt | |
| 2005/0011282 A1 | 1/2005 | Voege et al. | |
| 2007/0149922 A1 | 6/2007 | Schneider et al. | |
| 2008/0138842 A1 | 6/2008 | Boehringer | |
| 2008/0154183 A1 | 6/2008 | Baker et al. | |
| 2008/0183128 A1 | 7/2008 | Morriss et al. | |
| 2008/0221507 A1 | 9/2008 | Hoke et al. | |
| 2008/0312674 A1 * | 12/2008 | Chen | A61M 1/0058 606/162 |
| 2009/0104690 A1 | 4/2009 | Bayliff et al. | |
| 2009/0197283 A1 | 8/2009 | Gold | |
| 2009/0281483 A1 | 11/2009 | Baker et al. | |
| 2009/0281485 A1 * | 11/2009 | Baker | A61M 1/0058 604/35 |
| 2010/0016787 A1 | 1/2010 | Shapiro et al. | |
| 2010/0152653 A1 | 6/2010 | Hoke et al. | |
| 2011/0132369 A1 | 6/2011 | Sanchez | |
| 2011/0144588 A1 | 6/2011 | Taylor et al. | |
| 2011/0220119 A1 | 9/2011 | Lowenstein et al. | |
| 2012/0179118 A1 | 7/2012 | Hair | |
| 2013/0012869 A1 | 1/2013 | Cha et al. | |
| 2013/0137598 A1 | 5/2013 | Verschoor | |
| 2013/0244314 A1 | 9/2013 | Yuki et al. | |
| 2014/0121592 A1 | 2/2014 | Rubin | |
| 2014/0200507 A1 | 7/2014 | Azeez | |
| 2014/0275857 A1 | 9/2014 | Toth et al. | |
| 2014/0371690 A1 | 12/2014 | Sprada et al. | |
| 2015/0118689 A1 | 4/2015 | Egan | |
| 2016/0303308 A1 | 10/2016 | Layer et al. | |
| 2016/0375192 A1 | 12/2016 | Rubin et al. | |

FOREIGN PATENT DOCUMENTS

| | | | |
|---|---|---|---|
| EP | 2389918 A1 * | 11/2011 | A61H 35/04 |
| EP | 2389918 A1 | 11/2011 | |
| EP | 2914312 B1 | 8/2017 | |
| JP | 2010520033 | 6/2010 | |
| JP | 2010527636 | 8/2010 | |
| WO | WO2008058160 | 5/2008 | |
| WO | WO2008109726 | 9/2008 | |
| WO | WO2010126586 | 11/2010 | |
| WO | WO 2011/127407 | 10/2011 | |
| WO | WO 2014/070854 | 5/2014 | |
| WO | WO 2015/123276 | 8/2015 | |

OTHER PUBLICATIONS

Carrasquilla, et al; Chemistry a European Journal Communication, "Patterned Paper Sensors Printed with Long-Chain DNA Aptamers" 2015, 21, 7369-7373, Wiley Online Library.

Liu, et al; Angewandte Chemie, "Target-Induced and Equipment-Free DNA Amplification With a Simple Paper Device" 2016, 128, 2759-2763, Wiley Online Library.

* cited by examiner

IRRIGATION ASSEMBLY

CLAIM OF PRIORITY

The present application is a continuation-in-part application of U.S. application Ser. No. 13/664,034, filed on Oct. 30, 2012, which matured into U.S. Pat. No. 9,433,724 on Sep. 6, 2016, incorporated herein by reference.

FIELD OF THE INVENTION

This invention is directed to an irrigation assembly having a housing which includes an applicator and a cooperatively structured activating assembly operative for concurrent irrigation and aspiration or drainage of each nostril, independently of one another, in a manner which facilitates cleaning and disinfection of an individual's nasal cavity. Upon activation, irrigating fluid is delivered through a plurality of applicator nozzles, having an orientation which delivers the irrigating fluid into the selected nostril in a preferred pattern. Concurrently, aspiration or drainage of waste fluid and collected material from each nostril occurs by applying negative pressure through the applicator, resulting in the waste fluid being removed from the nostril and collected within the housing for subsequent disposal.

BACKGROUND OF THE INVENTION

Poor nasal hygiene is a common problem existing and prevalent in individuals of all ages and can lead to nasal and sinus disease. Such disease, including congestion, infection, and other pathologic conditions of the nasal passages and paranasal sinuses, is typically caused by viruses, bacteria and other microbes and/or exposure to environmental allergens. Sinonasal disease is one of the most common medical conditions in the United States, afflicting approximately 33 million people and accounting for over $5.8 billion in healthcare costs annually ("Nasal Congestion: More than physical obstruction," Science Daily, Oct. 17, 2011). Nasal congestion and the associated feeling of obstruction is the symptom that typically causes individuals to seek medical assistance. Common signs and symptoms arising from poor nasal hygiene include nasal inflammation, rhinorrhea, sinusitis, irritation, pain and nasal passage blockage. Medications used to treat nasal pathology inherently include potential side effects and possibly excessive costs.

A number of studies demonstrate that regular use of nasal irrigation is an effective therapy in the relief of symptoms associated with poor nasal hygiene (e.g. Rabago et. al, Journal of Family Practice. 2002; 51(12):1049-1055; Tomooka et. al, Laryngoscope. 2000 July; 110(7):1189-93.) Other similarly related clinical studies indicate that nasal wash with isotonic saline can improve certain infection outcomes (Slapak et. al, Archives of Otolaryngology-Head & Neck Surgery. 2008; January; 134(1):67-74) and that regular nasal irrigation is a beneficial therapy for the treatment of allergy related symptoms (e.g. Garavello et. al, Pediatr Allergy Immunol. 2003 April; 14(2):140-3.) Accordingly, these studies indicate that nasal irrigation is a clinically proven method of improving sinus related disease, including allergies and infections. Current standard of care for nasal irrigation involves exposing the nasal cavity and passages to a streaming volume of saline or other prophylactic or therapeutic solutions. In addition to cleansing the nasal cavities of pathogens and allergens, such irrigation related treatment is also believed to include a number of physiological effects. These include stimulation of mucosal cilia and increasing physiologic flow of mucous, which individually or in concert may reduce the risk of nasopharyngeal and sinus localization of pathogens and allergens, thereby reducing potential morbidity and mortality. Further, irrigation therapy that includes rinsing of the interior of the nasal cavity, typically washes away waste, microbial by-products, and/or encrustations, which may be the causal factor in a number of undesirable conditions and symptoms. Conventional irrigation techniques are intended to keep sinus cavities, nasal passages, and the drainage from sinuses to nasal passage in a healthy state. Improving nasal hygiene with irrigation thus reduces the likelihood that the nasal cavity, paranasal sinuses, and related structures will become colonized with pathogens, thereby reducing the potential for morbidity and mortality.

As conventionally practiced, nasal irrigation is known to apply and utilize various types of manually or automatically operated irrigation and/or nasal aspirators. As such, irrigating fluid is applied in a manner or in such volume sufficient to flood the nasal cavity in an attempt to remove the aforementioned pathogens, allergens, encrustations, or waste after the application of the irrigating fluid has been completed. However, disadvantages at least partially associated with the flooding of the nasal cavity, occur when the irrigating and aspirating steps are conducted separately or successively, which can lead to suboptimal cleansing and disinfection. As typically operated, existing manual devices serve to sequentially, rather than simultaneously, deliver irrigation agent to the nasal cavity followed by a subsequent and frequently delayed aspiration of the agent and accumulated waste.

Additionally, irrigation devices that flood the nasal cavity and sinuses can create a cumbersome, uncomfortable, and aesthetically unappealing experience for the user. For example, the flooding irrigant may create a drowning sensation for the user and waste fluid may travel around the nasal septum and drain out the same or opposite nostril, thereby spilling waste fluid onto a user's face and/or clothes. In flooding of the nasal passage a user may also experience the unpleasant taste of irrigant in the back of their throat. These devices are therefore unacceptable to many users and observers.

On the other end of the spectrum, irrigation/suction devices that do not flood the nasal cavity often infuse minimal fluids, typically in a mist that is insufficient to remove encrustations and other contaminants.

Other manual irrigation devices frequently involve the use of a conventionally structured bulb-type syringe. The ineffectiveness of such devices are well known and recognized as being generally associated with inadequate negative pressure and resulting inadequate removal of the waste fluid and waste materials contained within the nasal cavity or passages. Also, manual irrigation and suction devices may include dimensional and/or configurational characteristics which could possibly result in damage to the interior of the nasal cavity.

Irrigation devices that do not solely moisten the mucosa and provide sufficient flow to dislodge encrustations and contaminants (e.g. the neti pot and many commercially available nasal irrigation devices), require fluid to be added to the device from an external source, often tap water or bottled water. Such water may be contaminated with pathogenic microbes or other agents that can be infused into the nasal cavity and sinuses and cause infections, even death ("Primary Amebic Meningoencephalitis Deaths Associated With Sinus Irrigation Using Contaminated Tap Water", Yoder, et. al, Journal of Clinical Infectious Diseases, Aug.

22, 2012, Epub ahead of print). In addition, prior to irrigation, such fluid often needs to be manually mixed with a salt powder or other solute which can be time consuming and inconvenient.

For devices that interface with sealed fluid containers (U.S. Pat. No. 7,981,077) that are manually opened and fastened to the device, the manual attachment of the container can also cause inadvertent contamination. Also, because of suboptimal use of space within device housings, devices that collect waste fluid either capture only a small volume of such fluid or capture a larger volume of waste fluid, but do so at the expense of having to be unnecessarily bulky and require the presence of an additional collection reservoir.

Therefore, there is a need for an effective, convenient, efficient, and aesthetically pleasing irrigation assembly preferably in the form of a single pre-loaded, self contained, disposable device and/or a refillable device of similar attributes that can be infused with sterile or non-contaminated fluid. Moreover, such an irrigation assembly should be operative to accomplish delivery of an irrigating fluid, possibly including a cleaning, disinfecting, or other agent, to the nasal cavity and passages and the concurrent aspiration of the waste fluid and waste material there from. Concurrent irrigation and aspiration would then overcome many of the problems of existing devices and serve to effectively provide both a sufficient pressure applied to the irrigating fluid and a significant negative pressure applied to the waste fluid to better accomplish an improved irrigation therapy.

In addition, collecting waste fluid in the same reservoir as storage of clean irrigant, without contamination of clean irrigant, would overcome dimensional and configurational restrictions or physical characteristics, facilitate operation of the device in a safe and efficient manner, deliver clean solution and retrieve waste fluid and contaminants in an aesthetically pleasing manner and with minimal residual waste fluid contacting a user's face or clothes, and would also allow collection of large sample volumes of fluid and elements removed from the nasal passage for laboratory analytical testing. Such a proposed and preferred irrigation assembly may be a single use, disposable device or otherwise structurally modified to facilitate multiple or repeated uses by the replenishment of pre-loaded refills of the irrigating fluid, or refills from an external reservoir that hygienically maintains fluid, prior to eventual disposal. Although the mechanics of the device enable negative pressure, the ability to optionally drain waste fluid directly out the bottom of the device (i.e. gravity drain) would also accomplish the goal of an aesthetically pleasing and comfortable nasal irrigation process.

SUMMARY OF THE INVENTION

The present invention is directed to an assembly structured for the concurrent irrigation and aspiration of an individual's nasal cavity and passages in order to promote and maintain better nasal hygiene by effectively cleaning, disinfecting and/or medicating the nasal cavity and passages. More specifically, the irrigation assembly comprises a housing having an at least partially hollow interior of sufficient dimension and configuration to include a supply container therein. The supply container may be in a tubular or barrel like configuration at least partially similar in shape, structure and operation to the barrel of a syringe. Of course, additional shapes, including a square, triangle, oval or other shape may be equally effective.

Moreover, the interior of the supply container defines a chamber in which irrigating fluid is removably retained for eventual delivery to the nasal cavity. In addition, at least one embodiment comprises the supply container being prefilled or preloaded with an irrigating fluid which may affect the cleaning, as well as the disinfecting, of the nasal cavity and passages, thereby facilitating the maintenance of healthful nasal hygiene. The aforementioned disinfecting capabilities can be accomplished by formulating the irrigating fluid to include an appropriate disinfecting agent such as, but not limited to, hydrogen peroxide, acetic acid, a chlorine based substance, etc. Similarly, appropriate medication may be included in or define the irrigating fluid. Accordingly, a variety of different conditions including, but not limited to, infections, allergies, etc. can be effectively treated and/or prevented through the utilization of the irrigation assembly of the present invention, in order to establish and maintain proper nasal hygiene.

An applicator is connected to the housing and is dimensioned and configured to be at least partially and separately inserted within each nostril of the nasal cavity. Moreover, the applicator includes dual or multiple passages or channels comprising at least a first passage and a second passage. As explained in greater detail hereinafter, the first and second passages of the applicator are structured, in cooperation with the other operative components of the assembly, to facilitate the concurrent delivery of the irrigating fluid through the first passage and the concurrent aspiration of waste fluid from the nasal cavity through the second passage. More specifically, the first passage of the applicator may comprise a first interior tube or conduit concentrically surrounded by the second passage. As such the second passage may be in the form of an outer tuber or conduit, disposed in coaxial relation to the inner tube or conduit. When the applicator is properly positioned for use, the outer open ends of both the first and second passages are inserted within the nasal cavity. As described in greater derail hereinafter, the applicator of the various preferred embodiments of the present invention is dimensioned and configured to be independently inserted in each of the nostrils. However, the applicator and/or an interface used therewith can be structured for the insertion in and irrigation of both nostrils at the same time.

The concurrent irrigation and aspiration of each nostril serves to prevent flooding of the nasal cavity, wherein such flooding is frequently recognized as being uncomfortable, messy, and/or unnecessary to accomplish beneficial nasal hygiene. Flooding of the nasal cavity is also selectively prevented by regulating the volume and/or the pressure of the irrigating fluid being delivered. Moreover, in order to accurately regulate the irrigating fluid in the manner described, at least one embodiment of the irrigation assembly may include an alarm, recorded voice prompt or other appropriate indicating facilities operative to provide a clear indication to a user, as to the volume, quantity, etc. of the irrigating fluid being administered, during each irrigating session.

One additional feature of the present invention includes each of a plurality of dispensing nozzles being formed in the outer or "delivery end" of the applicator. Moreover, each nozzle is disposed at preferably an angle of 5-45 degrees relative to the longitudinal center axis of the applicator. By virtue of this preferred angular orientation, the irrigating fluid or liquid will be dispensed concurrently from each of the dispensing nozzles in a predetermined dispensing pattern. In turn, a substantially or at least partially swirling or "vortex" flow of the irrigating fluid will occur as it exits the nozzles and impinges onto the interior surfaces of the nostril in which the applicator is inserted. Such a "vortex" configuration of the dispensing pattern and/or flow of the irrigating fluid will cause a beneficial cleaning of the interior surfaces of the nostril. In addition the swirling or vortex flow will result in a channeling or directing of the irrigating fluid, into a central portion of the nostril. As a result, the waste fluid and dislodged waste material will be more effectively retrieved by the applicator, as the concurrent irrigation and aspiration of the nostril continues.

The irrigation assembly of the present invention also includes an activating assembly comprising a drive member or plunger movably disposed within the interior chamber of the supply container in fluid sealing relation to the interior surfaces thereof. As such, the drive member or plunger serves to segregate the irrigating fluid located in a first section or upstream part of the chamber from an initially empty second section or downstream portion of the chamber. As used herein the terms "upstream" and "downstream" refers to the direction of travel of the plunger towards the applicator, as the irrigating fluid is forced from the interior chamber, by the plunger, into and through the applicator.

The activating assembly also preferably includes a biasing structure disposed to continuously force the drive member or plunger into a pressure applying, dispensing relation to the irrigating fluid. As a result, the irrigating fluid will be forced to flow from the interior chamber to and through the first passage of the applicator and therefrom separately into each nozzle, when fluid communication is selectively established between the interior of the chamber and the applicator. Accordingly, a valve assembly, which may be considered a part of the activating assembly or independent thereof, is selectively disposable between an initial closed position and an open position. When the valve assembly is selectively disposed in the open position, the first passage of the applicator communicates with the interior of the chamber and also with the irrigating fluid therein.

Due to the fact that the drive member or plunger is continuously maintained in biasing or other pressure applying relation to the irrigating fluid, a disposition of the valve assembly in the open position and the resulting fluid communication with the applicator, will serve to force the irrigating fluid through the open valve assembly into and through the applicator so as to irrigate the nasal cavity.

Additional structural and operative features which facilitate the aspiration or drainage of waste fluid from the nasal cavity concurrently to the irrigation thereof include the interior of the chamber of the supply container being at least partially isolated from the interior of the housing. This at least partially isolated interior chamber will result in the creation or generation of a negative pressure "downstream" of the plunger, as the plunger moves within the interior chamber in driving relation to the irrigating fluid. As a result, the irrigating fluid is forced to flow and be dispensed from the "upstream" part of the chamber to and through the applicator. Concurrently to such movement of the plunger and dispensing of the irrigating fluid, the volume of the downstream portion of the chamber will expand, thereby creating a vacuum or negative pressure within the downstream portion. Such negative pressure will be communicated to and along a path of travel of the waste fluid existing between the second passage of the applicator and the interior of the chamber, as will be explained in greater detail hereinafter. Accordingly, the negative pressure communicated to the second passage will facilitate the removal of the waste fluid from the nasal cavity concurrently to the aforementioned forced flow of irrigating fluid into the nasal cavity through the first passage of the applicator.

It is emphasized, that as used herein the term "aspiration" or equivalent thereof is to be broadly interpreted and is used to describe the drainage and/or removal of the waste fluid and/or waste particles from the nasal cavity be irrigated. As such the removal of such waste fluid may be due to the resulting vacuum or negative pressure originating in the downstream portion of the chamber upon movement of the plunger within the chamber, as set forth above. Alternatively and/or in cooperation therewith, the removal of the waste fluid may be at least partially due to gravity and/or a build up of excess fluid in the nasal cavity, due to the concurrently conducted irrigation.

In order to facilitate communication of the negative pressure between the interior of the chamber and the aforementioned path of travel, a venting structure is provided. In at least one embodiment, the venting structure is disposed in fluid communication between the downstream section of the chamber and the interior of the housing. More specifically, a spacing is provided between the exterior surface of the supply container and the interior surface of the housing. This interior spacing may be defined as the aforementioned "path of travel" of the waste fluid as it is being aspirated or drained from the nasal cavity. In more specific terms, the second passage of the applicator is disposed in fluid communication with the path of travel and accordingly the aforementioned venting structure serves to communicate the created negative pressure within the downstream section of the chamber to the path of travel. Therefore there will be an at least minimal, but sufficient, vacuum or "pulling force" being exerted along the path of travel and interior of the second passage to facilitate removal of the waste fluid from the nasal cavity. Upon exiting the nasal cavity, the aspirated or drained waste fluid will pass through the second passage, along the path of travel, through the venting structure and into the interior of the downstream portion of the chamber of the fluid supply container.

Various preferred embodiments of the irrigation assembly of the present invention may therefore be structured as a single use, disposable device, wherein all or at a predetermined portion of the pre-stored or pre-loaded irrigating fluid will be utilized for a single application of the irrigating fluid into each nostril. In contrast, the housing and the supply container may be made larger, such that the irrigation assembly may be used for multiple applications. As should be apparent, repeated use of the irrigation assembly would necessitate that the initially stored quantity of the irrigating fluid be sufficient to permit its repeated use. In this latter embodiment, manipulation of the aforementioned valve assembly will regulate a forced flow or dispensing of an intended or predetermined amount of the irrigating fluid from the interior of the chamber of the supply container, as the valve assembly is selectively moved between the closed and open positions. In order to assure a proper or intended amount of irrigating fluid is administered to each nostril, the irrigation assembly may be structured to include audible or visual alarm or indicating capabilities. Such indicating capabilities may be "time based" or "volume based", wherein an adequate signal, indicator, etc. would be conveyed to a user, based respectively on the time duration of each administration of irrigating fluid or the quantity of irrigating fluid being administered.

After multiple applications and subsequent to dispensing all of the irrigating fluid, the irrigation assembly may be structured to replace the supply container with a new, pre-filled supply container or refill the container from an external reservoir that keeps the irrigating fluid sterile or clean and the reservoir sealed when not filling the container.

The external reservoir may be configured to attach to the device in an automated fashion where the user does not manually contact and potentially contaminate the irrigating fluid. As should be apparent, prior to refilling or attaching a new supply container the housing will be cleaned and the accumulated waste fluid and material will be removed. In an alternative, the original supply container may be refilled with an appropriate irrigating fluid, such as by the provision of an access port formed on the housing and/or supply container. With both of the above indicated "reusable" embodiments, the entire irrigation assembly may be discarded after a number of or of uses.

Yet additional structural and operative features of one or more preferred embodiments may include a drain structure including one or more emptying ports. Therefore, subsequent to the entry and/or collection of aspirated or drained waste fluid into the downstream section of the chamber, it may be removed or emptied to facilitate the repeated use of the irrigation assembly, after proper cleaning. Accordingly, the drain structure may be located in the bottom or other appropriate portion of the housing and in fluid communication with the interior of the downstream section of the chamber in which the waste fluid is collected. Further, the opening of the drain structure will allow the waste fluid to empty from the interior of the housing 12 or downstream section of the chamber, such that the irrigation assembly can be reused, as set forth above.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
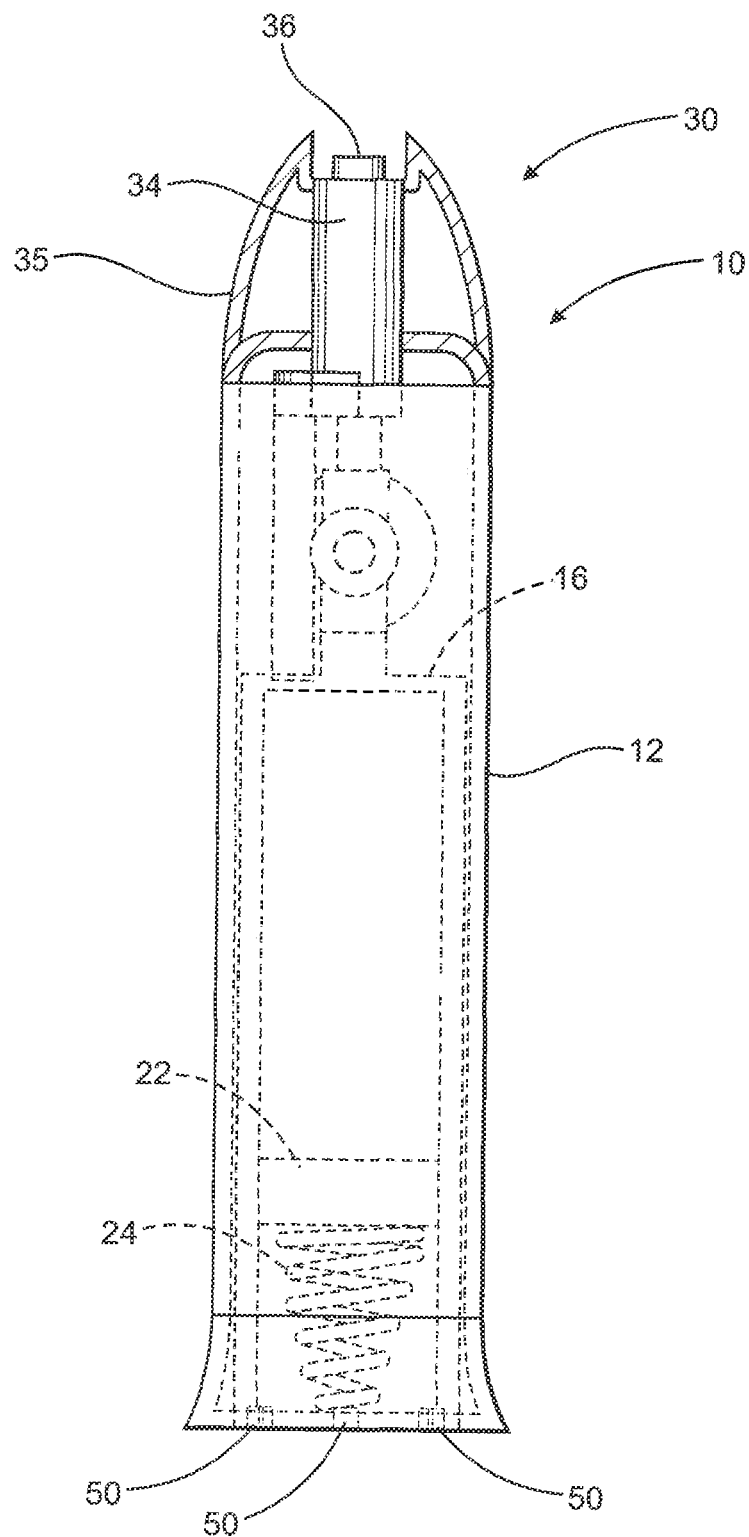
FIG. 1 is a front view in partial phantom of the irrigation assembly of the present invention.
Figure 2:
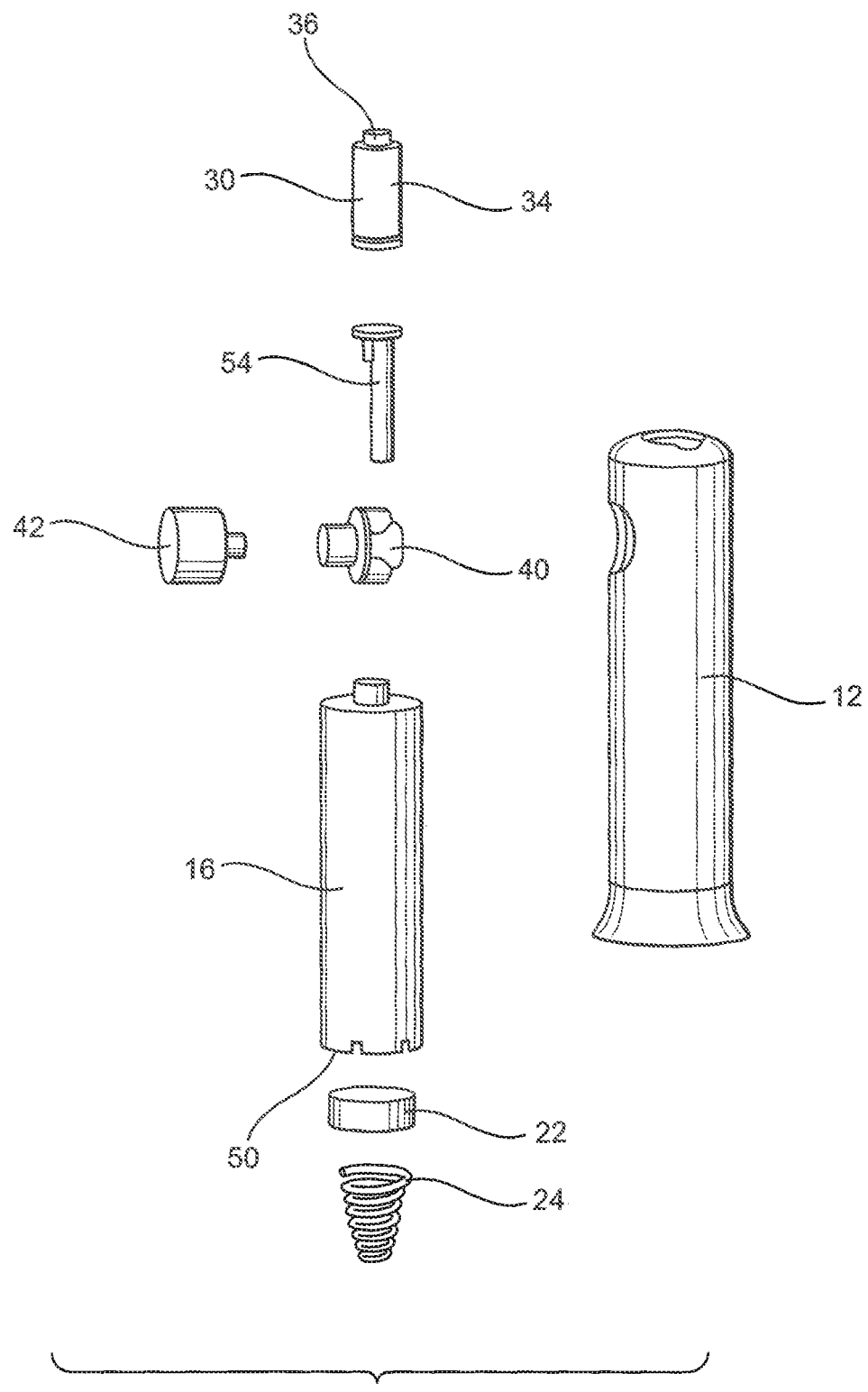
FIG. 2 is an exploded view of the various components of the assembled embodiment of FIG. 1.

As clearly represented in the accompanying drawings, the present invention is directed to an irrigation assembly generally indicated as 10, structured for concurrent irrigation and aspiration or drainage of an individual's nasal cavity and passages in order to promote and maintain better nasal hygiene by effectively cleaning, disinfecting and/or medicating the nasal cavity and passages.

More specifically, the irrigation assembly 10 comprises an outer housing 12 having an at least partially hollow interior 14. The interior 14 is sufficiently dimensioned and configured to include a supply container 16 disposed therein. Dependent upon the preferred embodiment and/or practical application of the irrigation assembly 10 being utilized, the supply container 16 may be fixedly/permanently and/or removably disposed within the interior 14. Moreover, the supply container 16 includes a chamber 18 disposed on the interior thereof, wherein at least a portion of the interior chamber 18 is structured to temporarily or removably retain an irrigating fluid 20 therein. The irrigating fluid 20 may be initially stored and eventually dispensed from what may be referred to as a first or upstream chamber section 18'. Also, a second or downstream chamber section 18" is disposed on the opposite side of a drive member or plunger 22, in fluid segregated relation to the upstream section 18'. The terms "upstream" and "downstream" 18' and 18" respectively refer to the direction of movement of the drive member or plunger 22 as the irrigating fluid 20 is being dispensed from the irrigation assembly 10. Therefore the plunger 22 is movably disposed within the interior chamber 18 in fluid sealing relation to the interior surfaces thereof.

For purposes of clarity and as will be explained in more detail with regard to the schematic representation of FIG. 4, the plunger 22 is associated with a biasing structure 24 which maintains the drive member or plunger 22 in a continuous, dispensing, "pressure applying" relation to the irrigating fluid 20. The pressure applying relation of the drive member or plunger 22 results in the forced flow and eventual dispensing of the irrigating fluid 20 from the first or upstream section 18' of the chamber 18, as indicated by the directional arrow 100. Accordingly, as the plunger 22 is forced to move within the interior of the chamber 18, due to the biasing influence of the biasing member 24, the irrigating fluid 20 will be forced to flow from the first or upstream section 18' in the direction corresponding to arrow 100.

Moreover, movement of the plunger 22 within the chamber in a manner causing the forced flow 100 will result in the volume of the first section 18' being diminished as the irrigating fluid 20 is dispensed. Concurrently, the volume of the downstream or second section 18" of the interior chamber 18 will expand or increase, as the plunger 22 causes the forced flow 100 of the irrigating fluid 20. As a result, a negative pressure will be at least initially formed within the second section 18" due to a venting structure 50 facilitating the passage of fluid into the downstream or second section 18", from the interior of the housing 12. Further, the plunger 22 and the biasing structure 24 may be considered a part of an activating assembly which includes structural and operative features facilitating the dispensing or forced flow 100 of the irrigating fluid 20 from the interior chamber 18 and more specifically from the first or upstream section 18' thereof.

Figure 3:
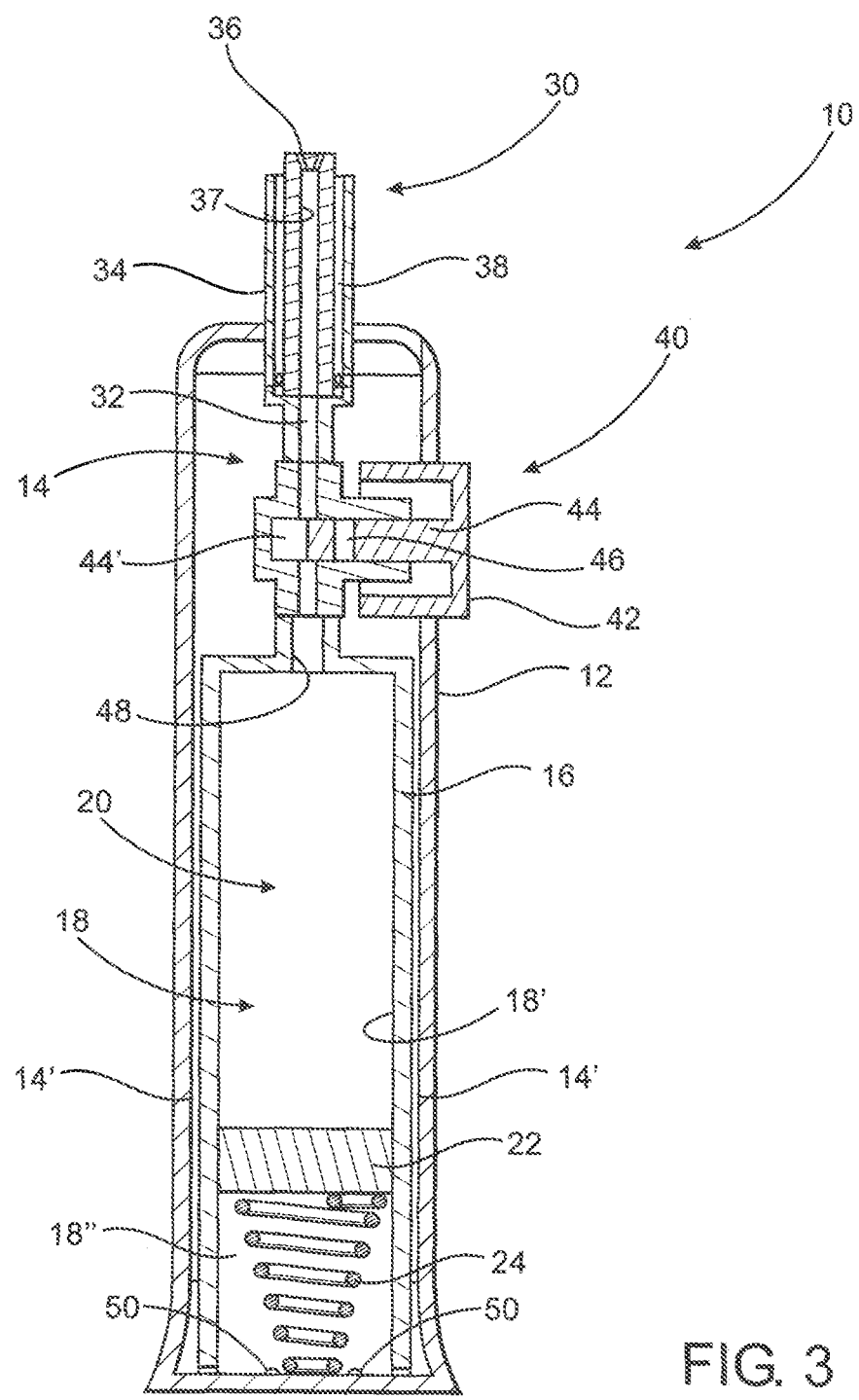
FIGS. 3 and 3A are interior, schematic side views of the embodiment of FIGS. 1 and 2.

Additional structural and operative features of the irrigation assembly 10 include an applicator generally indicated as 30. Applicator 30 is selectively disposable in fluid communication with the interior chamber section 18' as well as the irrigating fluid 20 initially stored or retained therein. Selective establishment of the fluid communication of the applicator 30 and the interior chamber 18 is accomplished through the selective manipulation of a valve assembly generally indicated as 40. In more specific terms, the valve assembly 40 includes an activating button or exteriorly accessible member 42. A valve stem 44 is connected to the button or member 42 which may be moved inwardly by applying a sufficient pushing or other appropriately directed force thereto. The valve assembly 40 may be initially disposed in a closed position as represented in FIG. 3, wherein fluid communication with the irrigating fluid 20 and the interior chamber 18 is blocked. As a result, the irrigating fluid 20 will be prevented from exiting the first chamber section 18' due to the position of a closed end 44' of the valve stem 44. However, a selective inward orientation or "pushing" of the member 42 will result in the valve assembly being in an open position. Such an open position of the valve assembly 40 has a valve port 46 of the valve assembly 40 being disposed in aligned, fluid communication with a delivery port 48 formed in the corresponding end of the supply container 16. Also the alignment of the valve port 46 and the delivery port 48 will serve to further establish fluid flow between the irrigating fluid 20 on the interior of the first or upstream section 18' and the inlet port 32 of the applicator 30.

As should be apparent, the resistance of a liquid to being compressed will result in the irrigating fluid 20, which will typically be in the form of a liquid, being maintained under a constant pressure as long as the valve assembly 40 is in the closed position. More specifically, while the valve assembly 40 is closed, the biasing structure 24 continuously forces the plunger 22 into pressure applying, driving relation to the irrigating fluid 20 in the form of a liquid. Accordingly, when the valve assembly 40 is subsequently disposed into the open position, the continuous force exerted on the irrigating fluid 20 by the plunger 22 and biasing structure 24 will result in the forced flow 100 of the irrigating fluid 20 from the upstream or first section 18' to the applicator 30, as set forth herein. Therefore, the irrigation assembly 10 can be made available with the irrigating fluid 20 pre-loaded into the first chamber section 18' and maintained therein under a sufficient pressure, while the valve assembly 40 is in the closed position, to eventually dispense the irrigating fluid from the first chamber section 18'. Therefore, when positioned for use, relative to the nasal cavity being irrigated, the irrigating fluid 20 will be "automatically" dispensed from the irrigation assembly 10, merely by disposing the valve assembly into the open position.

Figure 3A:
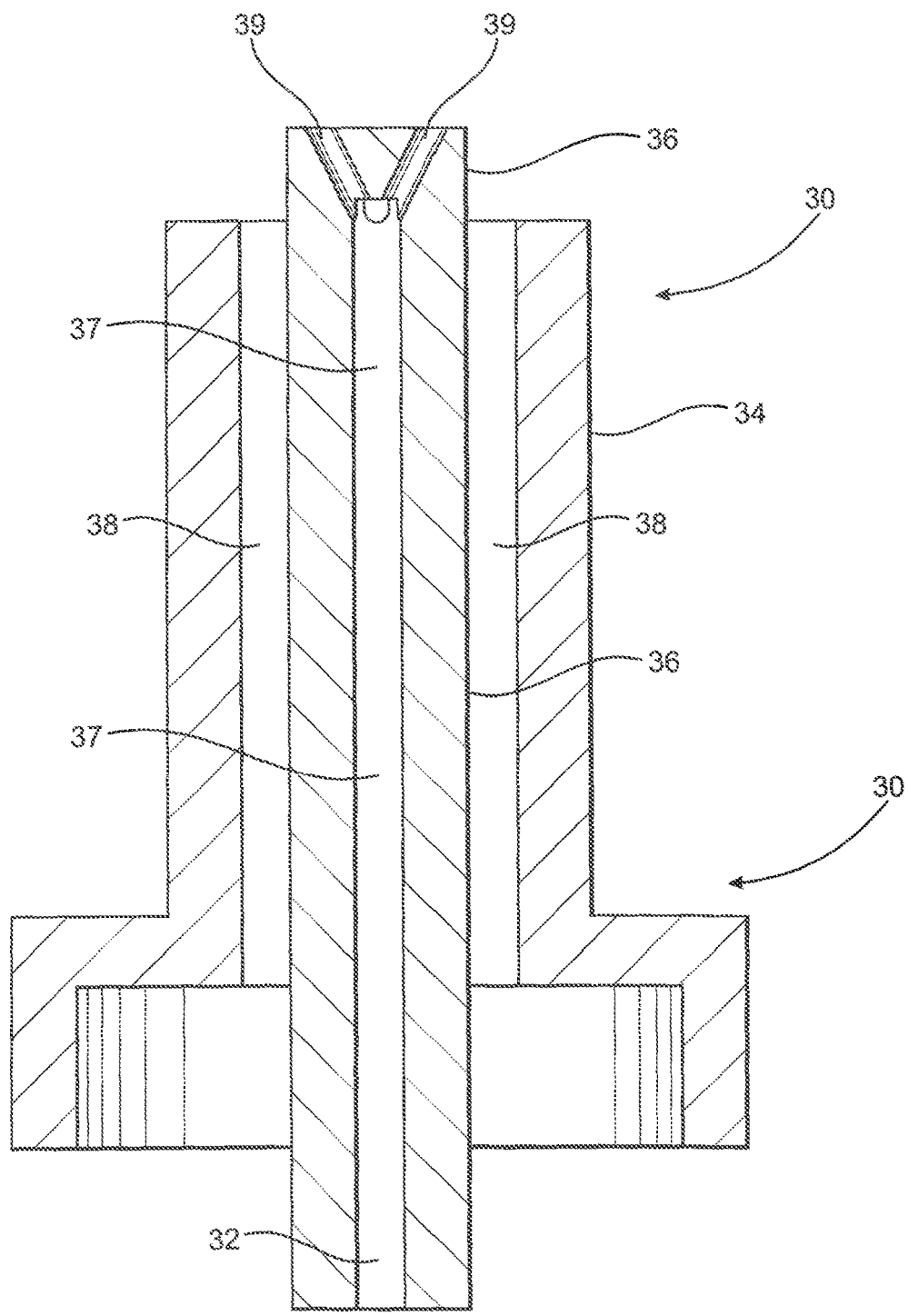

As represented in FIG. 3A, additional structural and operative features of one preferred embodiment of the applicator 30 include an outer tube or conduit 34 and an inner tube or conduit 36 disposed in coaxial, concentrically surrounded relation by the conduit 34. As such, the applicator 30 includes a first passage 37 extending along the interior of the inner tube or conduit 36. A second passage 38 is defined between the interior surface of the outer tube or conduit 34 and the exterior surface of the inner tube or conduit 36. As should be apparent from a review of the included Figures, the first passage 37 is disposed in direct fluid communication with the upstream or first section 18' of the chamber 18 as well as the irrigating fluid 20 therein, when the valve assembly 40 is in the aforementioned open position. Therefore, upon at least partial insertion of the applicator 30 into the nasal cavity, such as independently through each or a selected one of the open nostrils, both the first and second passages 37 and 38 will be at least partially disposed within and communicate with the interior of the nasal cavity. Furthermore, as illustrated in FIG. 1, a tip cover 35 is preferably provided as part of the applicator 30 to effectively seat the applicator 30 within the nostril, and also to preferably create an effective seal to prevent leakage and/or maximize the effects of any drainage or suction. In this regard, the tip cover 35 (see FIG. 1) preferably has a tapered configuration to provide for the effective insertion and seating within the nostril, and can be formed of a rigid material in view of the flexibility of the nostril to contour around the tip cover 35, and/or it may be partially resilient to provide some comfort and contouring.

The applicator 30 will then be properly positioned to begin and continue irrigating of the nasal cavity. When so positioned, the valve assembly 40 may then be disposed into the open position thereby creating the forced flow 100 of irrigating fluid 20 from the interior of the upstream section 18' and successively through the outlet port 48, valve port 46 and inlet port 32, into and through the passage 37, and out of the nozzles 39 into the interior of the nasal cavity. The forced flow 100 will be continuous due to the fact that the drive member or plunger 22 is under a continuously exerted dispensing, pressure applying force by the biasing structure 24.

While the biasing structure 24 may assume a variety of different structures and/or dispositions, one embodiment, as represented in the accompanying Figures, comprises it being disposed between a corresponding end 12' of the housing 12 and a correspondingly disposed surface 22' of the plunger 22. The physical characteristics of the biasing member 24 will be sufficient to force the plunger 22 along the length of the interior portion of the first or upstream section 18' of the interior chamber 18, thereby facilitating a dispensing of the irrigating fluid 20 therefrom into and through the applicator 30.

As emphasized, the structural and operative features of the irrigation assembly 10 are such as to accomplish an aspiration and/or drainage of the waste fluid from the nasal cavity concurrent to the delivery of irrigating fluid 20 thereto. Such concurrent aspiration and/or drainage is facilitated by a creation of an at least partial vacuum or negative pressure within the second or downstream section 18" of the interior chamber 18, as the plunger 22 moves along the length of the upstream section 18'.

Due to the provision of the venting structure 50, the interior of the chamber 18 is partially enclosed concurrently to the first and second chamber sections 18' and 18" being disposed in fluid segregating relation to one another by the plunger 22. As a result, movement of the plunger 22 in a direction towards the valve assembly 40, causing the forced flow of fluid 100, serves to diminish the volume and fluid content of the interior of the first or upstream section 18' concurrent to an increase or expansion of the volume of the second or downstream section 18". Of course, it is understood that other configurations, such as, including a flexible bladder segregated into the first and second chambers by a moveably clamping and/or segregating element, could also be effective to maintain the functionality of a single larger volume segregated into cooperative chambers that vary in size while maintaining the isolation of the irrigation fluid from contamination.

Figure 4:
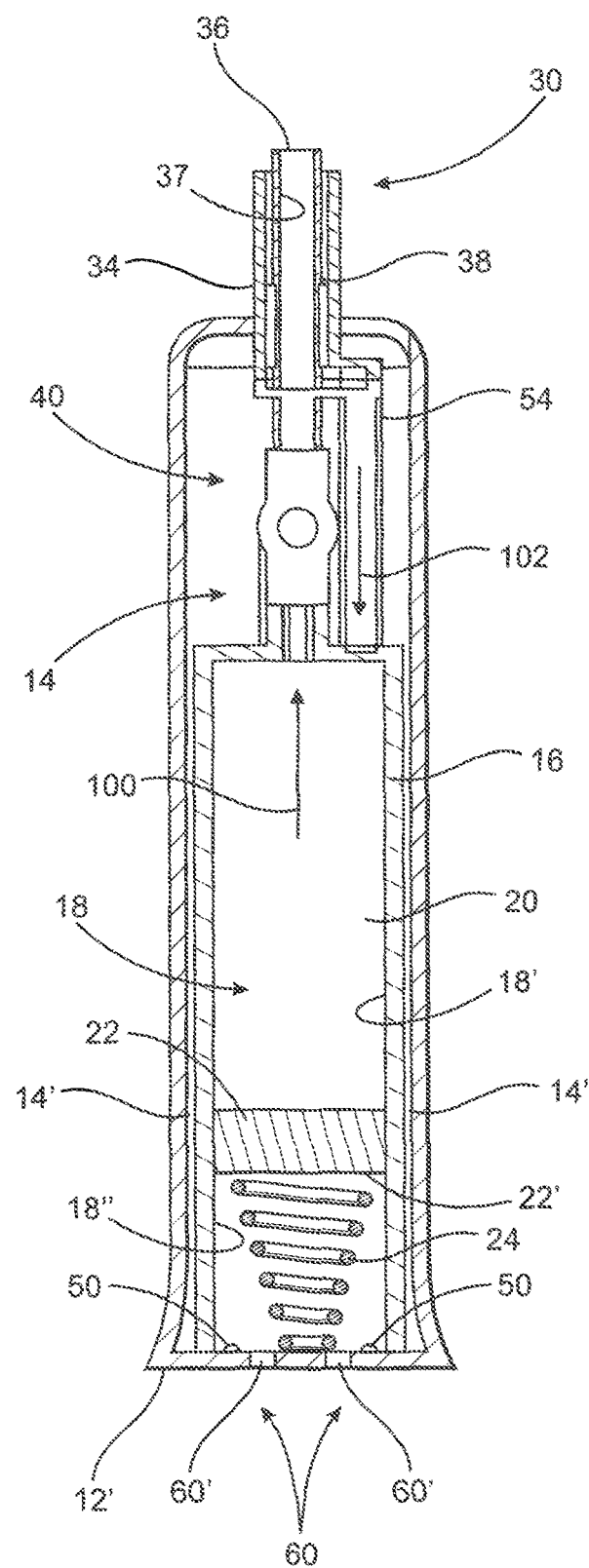
FIG. 4 is a schematic interior rear view of the embodiment of FIGS. 1 through 3.

As indicated in FIGS. 1 and 4, the venting structure 50 is preferably formed along the end of the supply container 16 which is opposed to the location of the valve assembly 40. Such venting structure 50 may include at least one or a plurality of individual, spaced apart vents, which are disposed in fluid communication between the interior of the downstream chamber section 18" and the interior 14 of the housing 12. More specifically the housing 12 and the supply container 16 are cooperatively dimensioned and configured to create a space 14' between the interior surface of the housing 12 and the exterior surface of the supply container 16. Such space 14' may be disposed in at least partially surrounding relation to the exterior of the supply container 16 as well as being disposed in fluid communication with the second passage 38 in the applicator 30 (see FIG. 3) by means of a connecting conduit or passage 54.

Therefore, the space 14' may at least partially define a path of travel of the aspirated waste fluid as it passes from the interior of the nasal cavity, through the second passage 38, along the interior of the connecting conduit or passage 54 into the space 14' and eventually into and through the vent structure 50 into the interior of the second or downstream section 18" of the chamber 18. For purposes of clarity, the flow and/or at least partial path of travel of the aspirated waste fluid is schematically represented by directional arrow 102 as it leaves the second passage 38 of the applicator 30 and begins to enter the portion of the path of travel defined by the space 14' between the interior and exterior surfaces of the housing 12 and the supply container 16 respectively. Moreover, the at least partial vacuum or negative pressure created or generated within the second or downstream section 18" of the chamber 18, by the movement of the drive member or plunger 20 as it causes the forced flow 100 of irrigating fluid 20, will be sufficient to create a "pulling force" which further facilitates the aspiration of the waste fluid from the nasal cavity concurrent to the introduction and of the irrigating fluid 20 into the nasal cavity through the first passage 37. The amount of aspirated waste fluid passing into the interior of the second section or downstream section 18" will be sufficient, due at least in part to the created vacuum or negative pressure, to empty the waste fluid from the nasal cavity in an effective manner.

As set forth above, the various preferred embodiments of the irrigation assembly 10 of the present invention may be structured as a single use, disposable device, wherein all or at a predetermined portion of the pre-stored or pre-loaded irrigating fluid will be utilized for a single application of the irrigating fluid into each nostril. In contrast, the housing 12 and the supply container 16 may be made larger, such that the irrigation assembly may be used for multiple applications. As should be apparent, repeated use of the irrigation assembly 10 would necessitate that the initially stored quantity of the irrigating fluid be sufficient to permit its repeated use. In this latter embodiment, manipulation of the aforementioned valve assembly 40 and drive member 22 will regulate a forced flow or dispensing of an intended or predetermined amount of the irrigating liquid from the interior of the upstream portion 18' of the chamber 18 of the supply container 16, as the valve assembly 40 is selectively moved between the closed and open positions. In order to assure a proper or intended amount of irrigating fluid is administered to each nostril, the irrigation assembly 10 may be structured to include audible or visual alarm. Such an alarm or other appropriate indicating capabilities may be "time based" or "volume based", wherein an adequate audible or visual signal would be conveyed to a user, based respectively on the time duration of each administration of irrigating fluid or the quantity of irrigating fluid being administered.

After multiple applications and subsequent to dispensing all of the irrigating fluid, the irrigation assembly 10 may be structured to replace the supply container 16 with a new, pre-filled supply container (not shown). As should be apparent, prior to refilling or attaching a new supply container 16 the housing 12 will be thoroughly cleaned and the accumulated waste fluid and material will be removed. In the alternative, the original supply container may be refilled with an appropriate irrigating fluid, such as by the provision of an access port formed on the housing and/or supply container. With both of the above indicated "reusable" embodiments, the entire irrigation assembly may be discarded as desired or after a predetermined number of uses.

Figure 5:
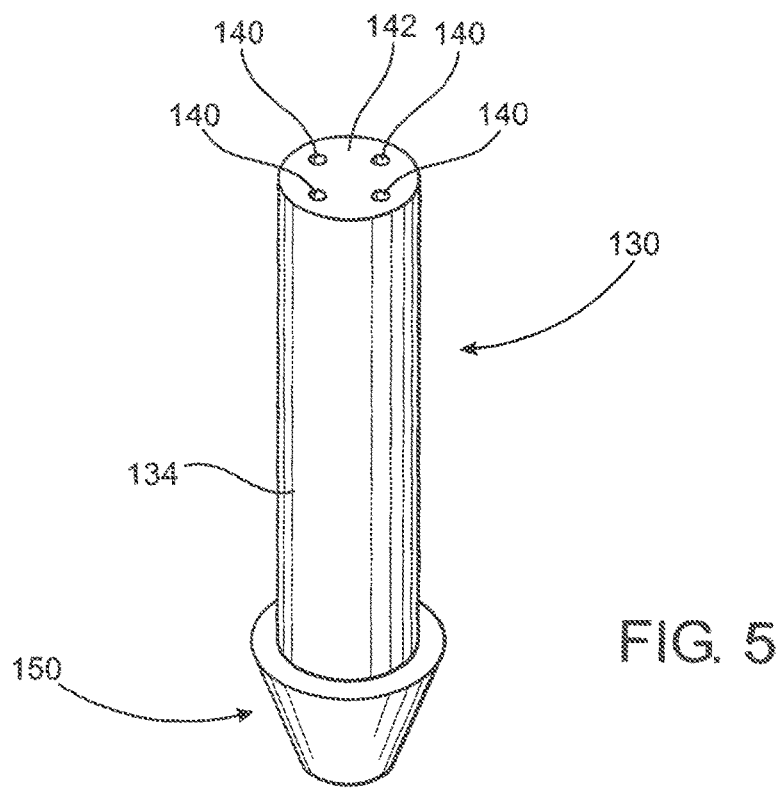
FIGS. 5 and 5A are perspective detail views of another preferred embodiment of an applicator component of the irrigation assembly of the present invention.
Figure 6:
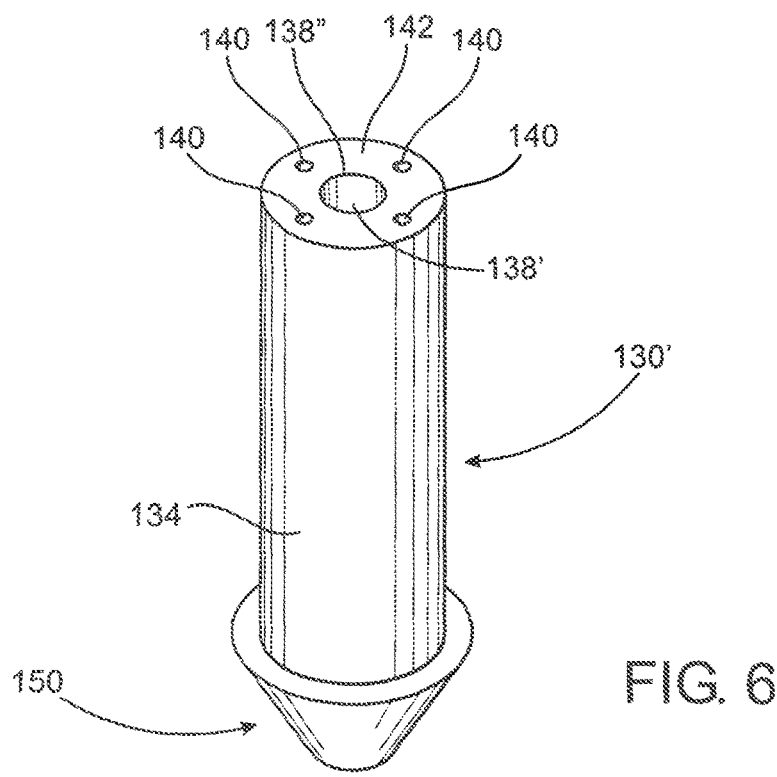
FIG. 6 is a perspective detail view of yet another embodiment of an applicator component similar to but distinguishable from the embodiment of FIGS. 5 and 5A.
Figure 5A:
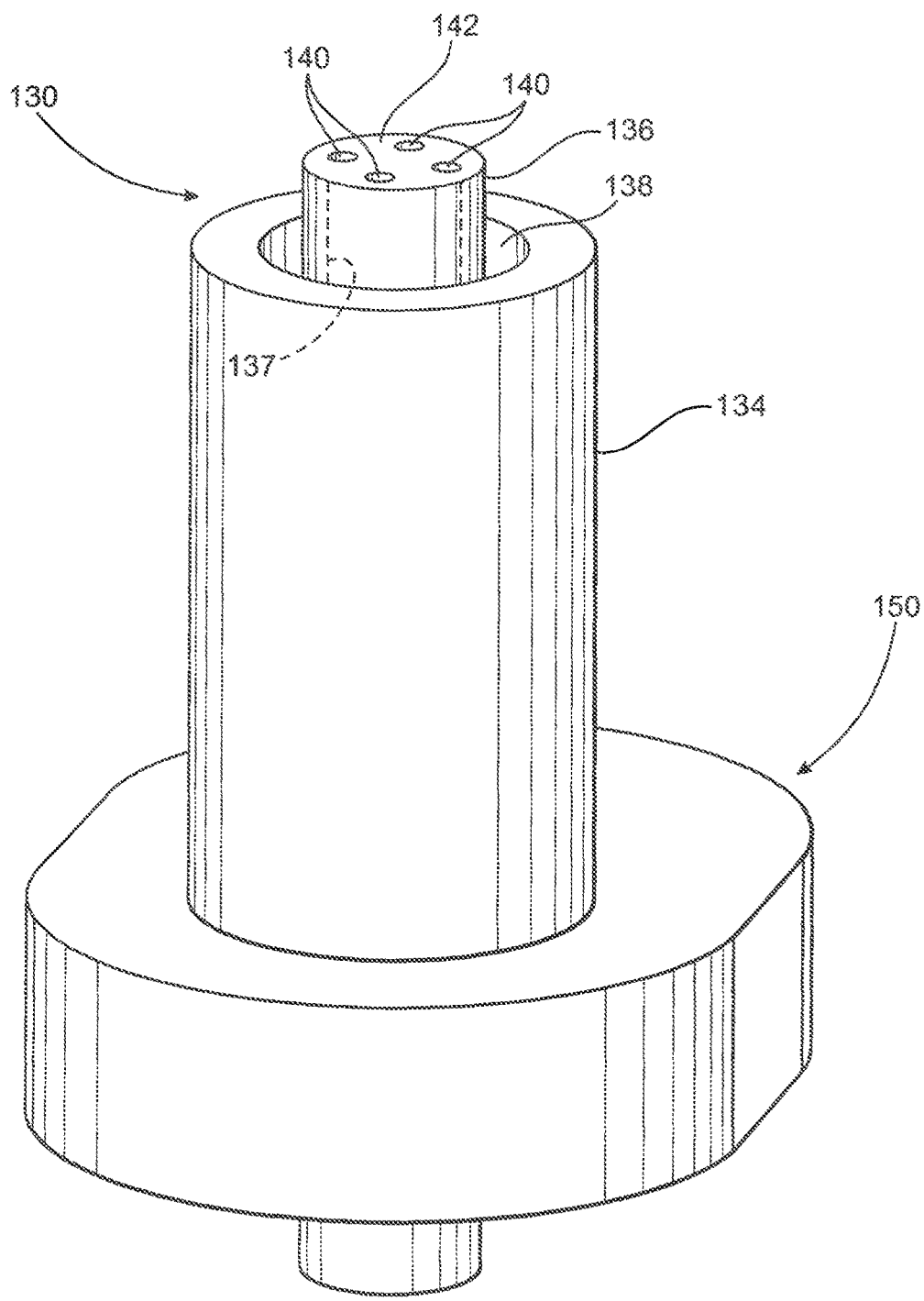
Figure 7:
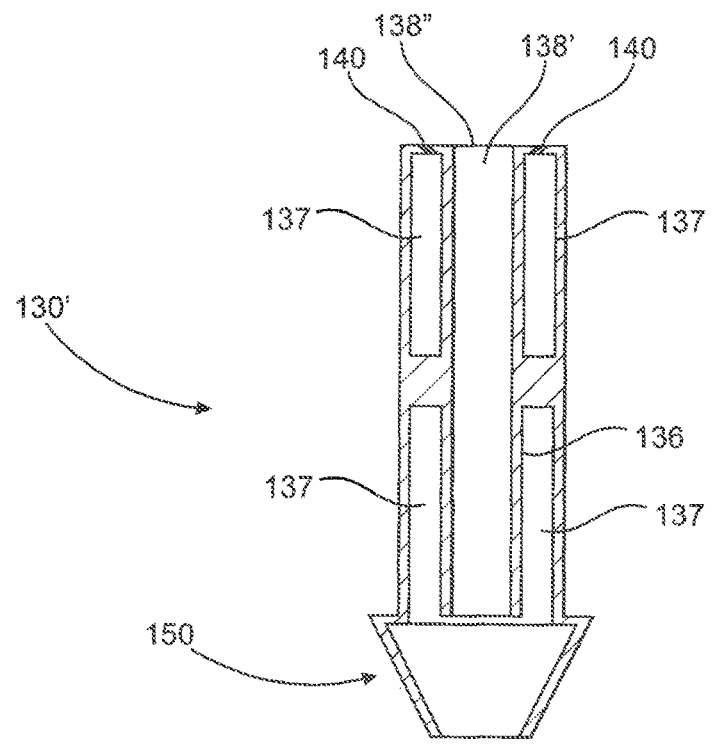
FIG. 7 is a longitudinal sectional view of the embodiment of FIG. 6.
Figure 8:
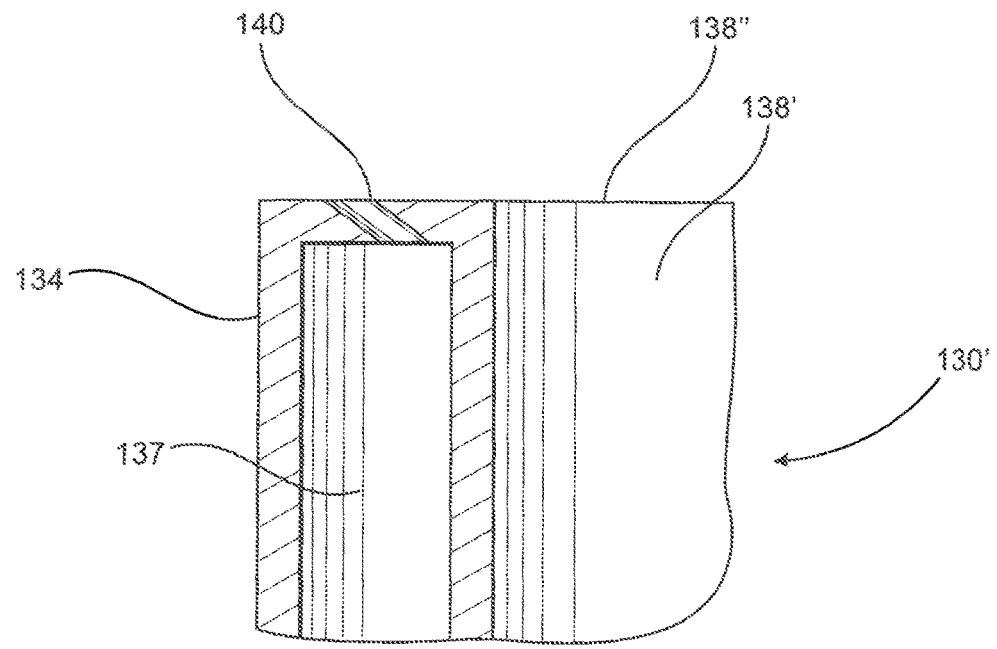
FIG. 8 is a detail cutaway view of the embodiment of FIGS. 6 and 7.
Figure 9:
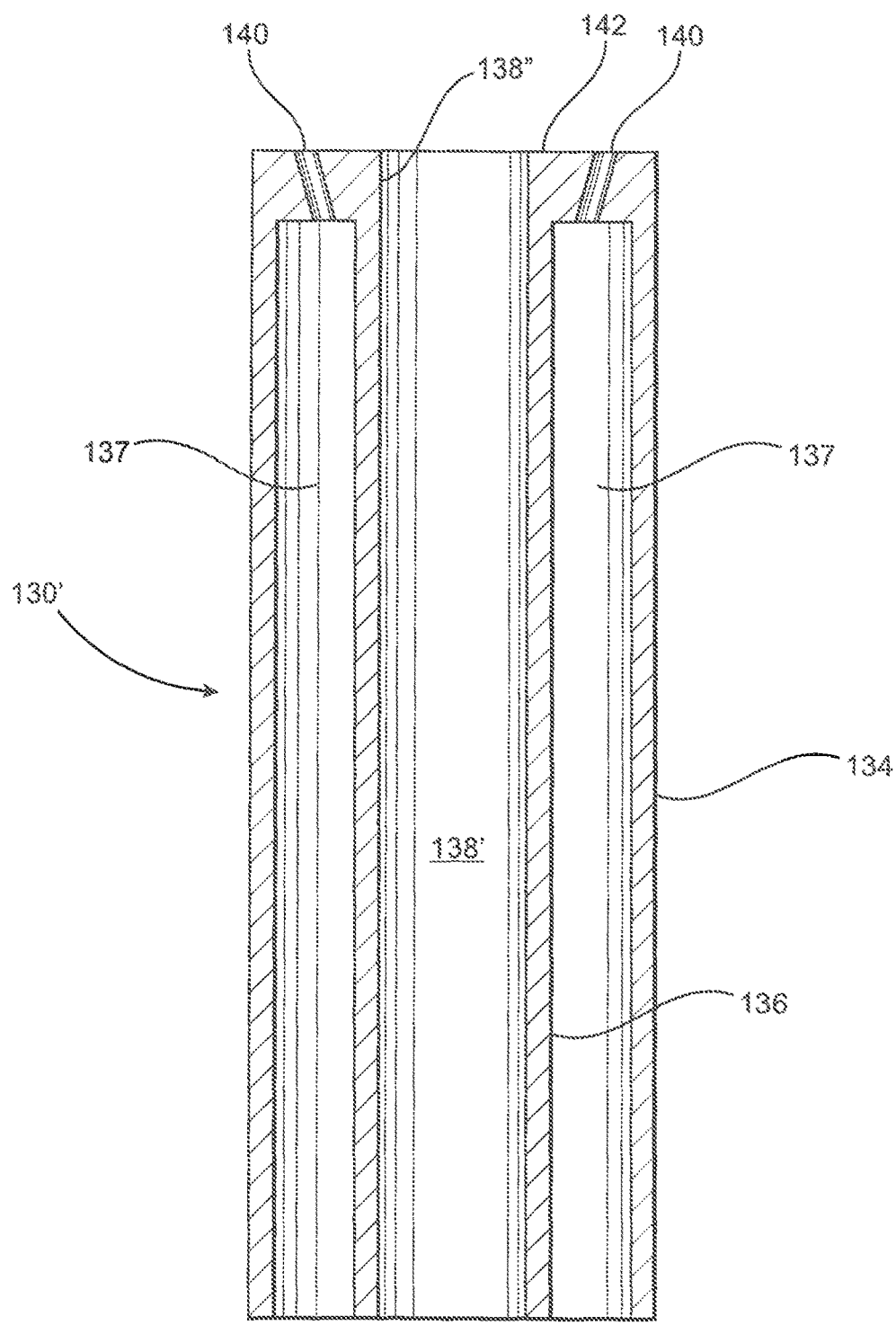
FIG. 9 is a schematic longitudinal detail view of the interior of the embodiment of FIGS. 7 and 8.
Figure 10:
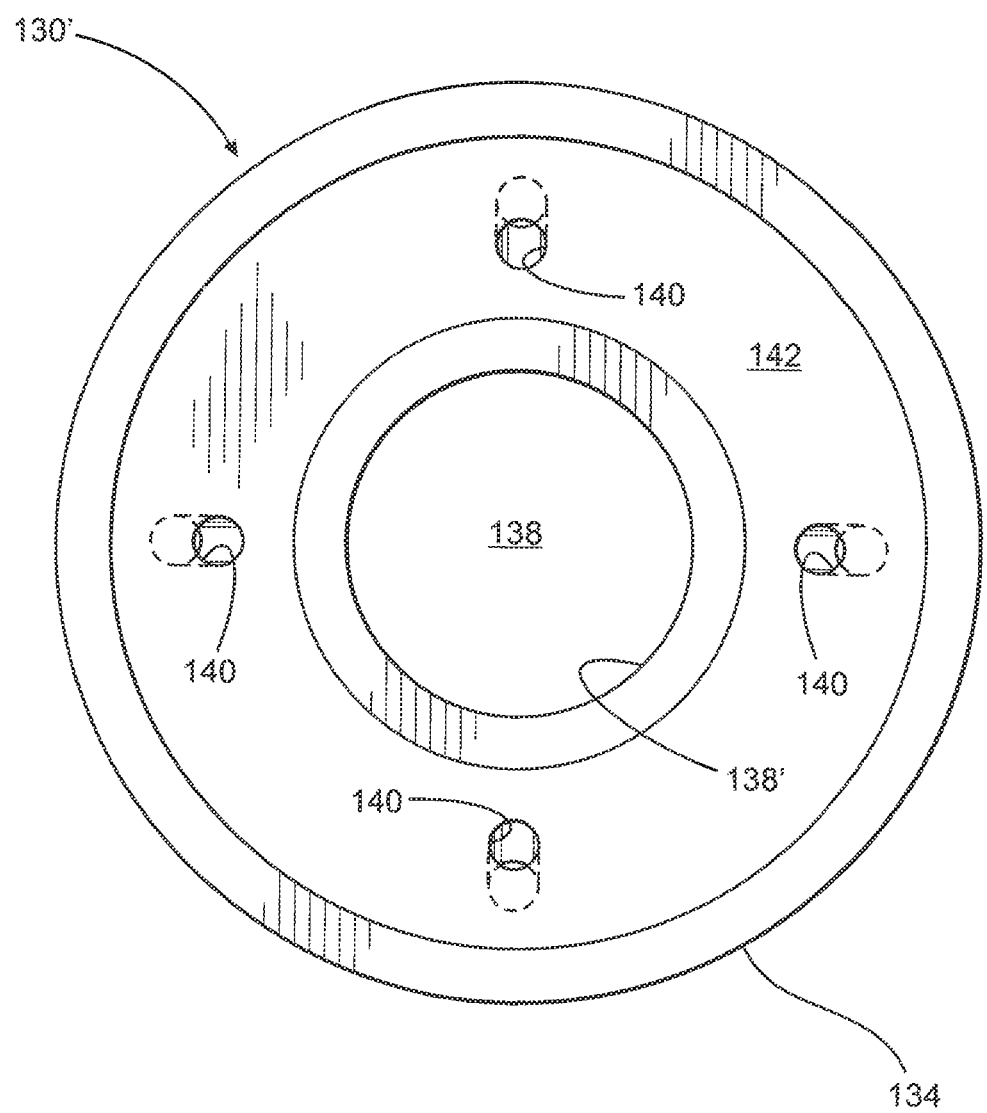
FIG. 10 is an end view of the embodiment of FIG. 9.
Figure 11:
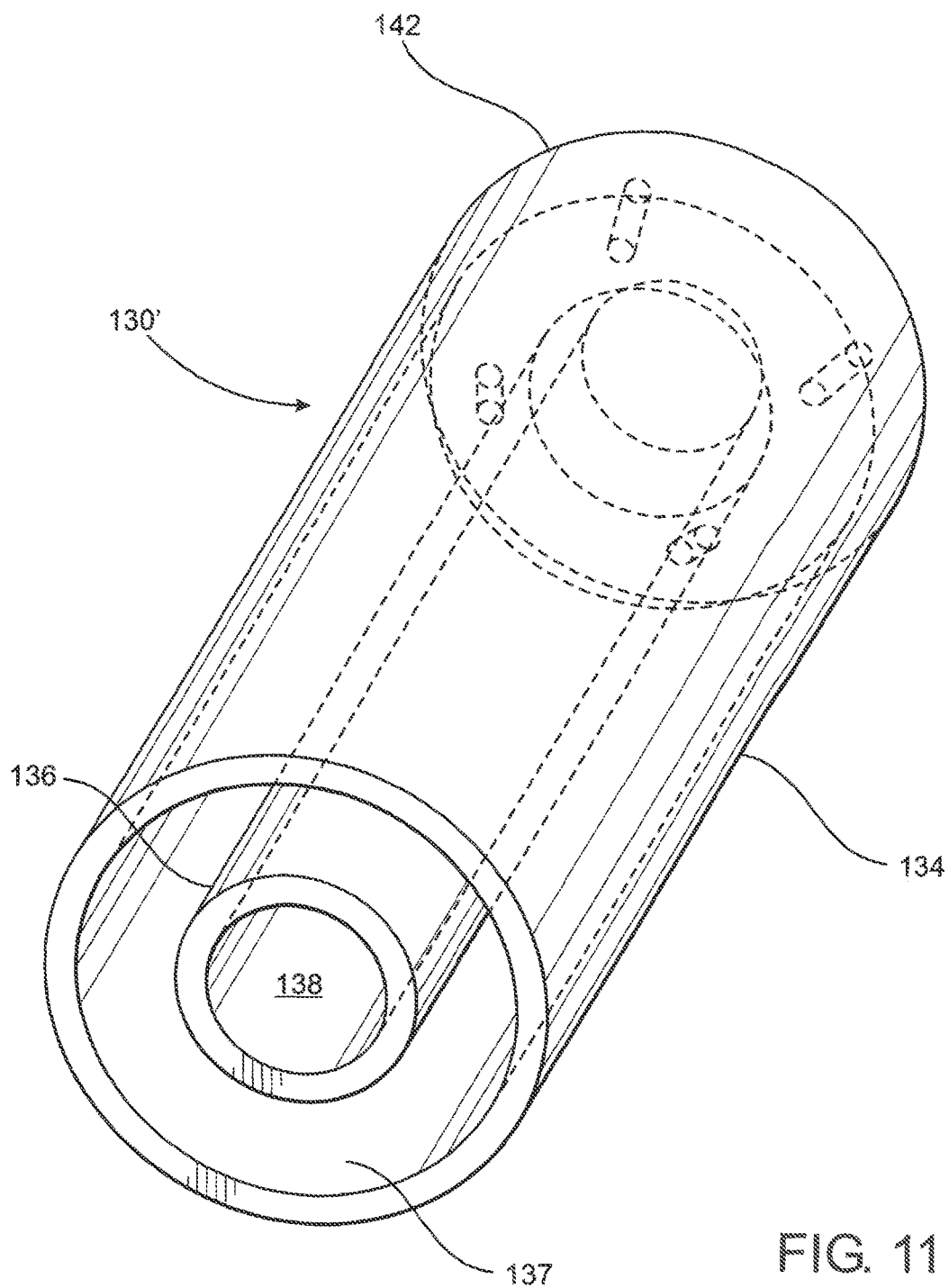
FIG. 11 is a perspective interior end view of the embodiment of the embodiment of FIGS. 9 and 10.

Additional preferred embodiments of the present invention include structural variations or modifications of the applicator 130 as represented in the embodiment of FIGS. 5, 5A and applicator 130' as represented in the embodiment of FIGS. 6 through 11. Both of the applicators 130 and 130' include a plurality of dispensing nozzles 140 formed in the outer or distal end 142 of each of the applicators 130 and 130'. As clearly represented in FIGS. 8 and 9, each of the dispensing nozzles 140 are disposed at preferably an angle of between 5-45 degrees, relative to the longitudinal center axis of the corresponding applicator 130 or 130', with a preferred angle of generally about 15 degrees. The irrigating liquid will be dispensed concurrently from each of the dispensing nozzles 140. As such, the aforementioned angular orientation of the dispensing nozzle 140 defines a predetermined dispensing pattern resulting in a substantially or at least partially swirling or "vortex" flow of the irrigating fluid as it exits the nozzles 140 and impinges onto the interior surfaces of the nostril in which the applicator 130, 130' is inserted. Such a "vortex" configuration of the dispensing pattern and/or flow of the irrigating fluid will cause a thorough cleaning of the interior surfaces of the nostril. In addition the swirling or vortex flow will result in a channeling or directing of the irrigating fluid, into a central portion of the nostril. As a result, the waste fluid and dislodged waste material will be more effectively retrieved by the applicator, as the concurrent irrigation and aspiration/drainage of the nostril is performed.

In the embodiment of FIGS. 5 and 5A, the dispensing nozzles 140 are disposed in communicating relation with a first passage 137, functionally equivalent to the first passage 37, represented in FIGS. 3, 3A and 4. As such, the irrigating liquid or fluid passes through the first passage 137 from the upstream chamber 18' and will exit through the dispensing nozzles 140 into the nostril engaged by the applicator 130. Moreover, as represented in FIG. 5A the second passage 138 is concentric to and located exteriorly of the first passage 137 and between the exterior surface of the inner conduit 136 and the inner surface of the outer conduit 134. Accordingly, similar to the embodiment of FIGS. 3, 3A and 4, a first passage 137 is disposed on the interior of the inner conduit 136 and in direct fluid communication with each of the plurality of dispensing nozzles 140. The drainage or aspiration of the waste fluid, once having performed a cleaning action on the interior surfaces of the nostril, will then return to the interior of the housing 12 by virtue of flow along the second passage 138.

In contrast, the applicator 130' of the embodiment of FIGS. 6 through 11 includes the first passage 137 again being disposed in direct fluid communication with each of the dispensing nozzles 140 and with the upstream chamber or section 18' of the supply container 16 through the valve assembly 40. However, in the applicator 130' the first passage 137 is located exteriorly of a second passage or drain passage 138'. The drain and/or second passage 138' is disposed interiorly and coaxially to the center longitudinal axis of the applicator 130'. As indicated above, the "vortex" flow pattern of the irrigating fluid, as it issues and/or is dispensed from the angularly oriented dispensing nozzle 140, will result in a center channeling or directing of the irrigating fluid or waste fluid subsequent to an engaging of the interior surfaces of the nostril. As such, the centrally located second or drain passage 138' is disposed in an interior position within the inner conduit 136. This inner or substantially centralized location of the second passage 138' facilitates the collection, drainage and aspiration of the irrigating fluid and waste material (waste fluid) dislodged or collected from the interior of the nostril to the interior of the housing, along the channel 14', as set forth above with regard to the embodiments of FIGS. 3 and 4. As also clearly represented, the drain passage or second passage 138' includes an open outer or distal end 138" which further facilitates the drainage, aspiration and/or removal of the irrigating fluid, once having performed its cleaning, disinfecting and/or medicating function of the interior of the nostril being treated.

Additional structural features include a mounting or connecting end generally indicated as 150, which may assume a variety of different dimensions and configurations to facilitate the attachment of the applicators 130 or 130' to the remainder of the components of the irrigating assembly 10. Such attachment of the applicators 130 and 130' will establish their fluid communication with the upstream chamber section 18', valve assembly 40 and interior passage 14' of the housing 12.

Yet additional structural and operative features of one or more preferred embodiments may include a drain structure 60 including one or more emptying ports 60', as represented in FIG. 4. In an embodiment incorporating the drain structure 60, the irrigation assembly 10 may be repeatedly reused. More specifically, once the aspirated or drained waste fluid has been collected into the downstream section 18" of the chamber 18, the collected waste fluid may be removed or emptied from the housing 12 and/or chamber section 18" to facilitate the repeated use of the irrigation assembly 10, after proper cleaning. Accordingly, the drain structure 60 including the one or more emptying ports 60' may be located in the bottom 12', or other appropriate portion of the housing 12, in fluid communication with the interior of the downstream section 18' of the chamber 18 in which the waste fluid is collected. Further, the opening of the emptying ports 60' of the drain structure 60 will allow the collected waste fluid to empty from the interior of the housing or downstream section 18" of the chamber 18, such that the irrigation assembly can be repeatedly reused, as set forth above.

Accordingly and as set forth above, the irrigation assembly 10 may be a single use, disposable device or be structurally modified to facilitate multiple or repeated uses by the replacement of supply containers 16, pre-loaded with irrigating fluid. Alternatively, after emptying the waste fluid, such as through the drain structure 60, the supply container 16 and chamber 18 may be refilled from an external reservoir that hygienically maintains fluid, prior to refilling and use.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. An assembly structured for concurrent irrigation and drainage of a nasal cavity, said assembly comprising:
a housing including an interior chamber comprising a first chamber section and a second chamber section, said first chamber section structured to contain irrigating fluid therein,
a single applicator connected to said housing and comprising a first passage and a second passage disposed therein; said single applicator dimensioned and configured to be inserted in the nasal cavity through a single, common nostril,
said first passage and said second passage concurrently disposable in fluid communication with the nasal cavity through the single, common nostril;
said first passage at least partially defining a flow path of irrigating fluid from said first chamber section into the nasal cavity; said second passage at least partially defining a path of travel of a drained waste fluid from the nasal cavity into said second chamber section,
an activating assembly comprising at least a drive member structured to force the irrigating fluid from said first chamber section through said flow path, when said single applicator is in the single, common nostril,
said drive member movably disposed in segregating, fluid sealing relation between said first and second chamber sections;
said movement of said drive member into driving relation to the irrigating fluid comprising a concurrent reduction of said first chamber section and expansion of said second chamber section and a concurrent negative pressure being formed in said second chamber section and said path of travel; and
said concurrent negative pressure resulting in aspiration of the drained waste fluid, via said path of travel, from the nasal cavity concurrent to delivery of the irrigating fluid, via said flow path, to the nasal cavity, when said single applicator is disposed in the nasal cavity.

2. An assembly as recited in claim 1 further comprising a valve assembly disposable on the housing between an open position and a closed position; said open position defining a path of fluid flow of the irrigating fluid from said first chamber section to said flow path and the nasal cavity.

3. An assembly as recited in claim 2 wherein said activating assembly is cooperatively structured and disposed with said valve assembly to force the irrigating fluid from said first chamber section through said flow path, when said valve is in said open position.

4. An assembly as recited in claim 1 wherein said single applicator is dimensioned to be inserted into the nasal cavity through each nostril, separately from and independent of the other nostril.

5. An assembly as recited in claim 1 further comprising a drain structure formed in said housing and disposable in an emptying orientation, said emptying orientation defining fluid communication between said second chamber section and an exterior of said housing and an emptying of waste fluid from said interior chamber through said drain structure.

6. An assembly structured for concurrent irrigation and aspiration of a nasal cavity, said assembly comprising:
a housing including a supply container disposed therein,
said supply container including an interior chamber comprising a first chamber section and a second chamber section, said first chamber section structured to retain irrigating fluid therein,
an applicator connected to said housing; at least a portion of said applicator dimensioned and configured to be inserted in the nasal cavity,
said applicator comprising a first passage and a second passage; said first passage at least partially defining a flow path of irrigating fluid from said first chamber section into the nasal cavity; said second passage at least partially defining a path of travel of a drained waste fluid from the nasal cavity into said second chamber section, said path of travel extending in fluid communication with and between said second passage and said second chamber section and between an interior surface of said housing and an exterior surface of said supply container, a valve assembly disposable on the housing between an open position and a closed position; said open position defining a path of fluid flow from said first chamber section to said applicator and the nasal cavity, an activating assembly comprising a drive member disposed within said interior chamber and cooperatively structured with said valve assembly to force the irrigating fluid from said first chamber section through said applicator, when said valve assembly is in said open position, said drive member configured to force the irrigating fluid from said first chamber section through said applicator as a result of movement of said drive member corresponding to a reduction of said first chamber section and an expansion of said second chamber section and a concurrent negative pressure being formed in said second chamber section and said path of travel; and said concurrent negative pressure resulting in aspiration of the drained waste fluid, via said path of travel, from the nasal cavity into said second chamber section concurrent to delivery of the irrigating fluid from said first chamber section, via said flow path, to the nasal cavity when said applicator is disposed in the nasal cavity.

7. An assembly as recited in claim 6 wherein said drive member comprises a plunger movably disposed within said interior chamber in substantially fluid sealing relation with interior surfaces of said supply container, and said activating assembly further comprising a biasing structure structured to move said plunger to force the irrigating fluid from said interior chamber to and through said applicator when said valve assembly is in said open position.

8. An assembly as recited in claim 7 wherein said concurrent negative pressure formed within said path of fluid flow and said second chamber section upon movement of said plunger within said interior chamber and forced flow of the irrigating fluid from said first chamber section to and through said flow path.

* * * * *